United States Patent [19]

Muth et al.

[11] Patent Number: 4,925,621
[45] Date of Patent: May 15, 1990

[54] PRESSURE TUBE SAMPLING

[75] Inventors: Walter E. Muth, Pembroke; Roger Joynes, Deep River; Clair A. Cox, Chalk River; Brian A. Cheadle, Deep River; Don J. Burnett, Toronto; Han Adema, Burlington, all of Canada

[73] Assignee: Atomic Energy of Canada Limited, Ottawa, Canada

[21] Appl. No.: 275,017

[22] Filed: Nov. 22, 1988

[30] Foreign Application Priority Data

Nov. 23, 1987 [CA] Canada .................................. 552530

[51] Int. Cl.$^5$ ............................................. G21C 17/00
[52] U.S. Cl. ..................................... 376/262; 376/245; 73/864.41
[58] Field of Search ....................... 376/260, 245, 262; 73/864.41; 83/919

[56] References Cited

U.S. PATENT DOCUMENTS 2,826,077  3/1958  Walker .............................. 73/864.41
4,252,200  2/1981  Peterson ........................... 73/864.41
4,611,498  9/1986  Stahura ............................. 73/864.41

FOREIGN PATENT DOCUMENTS 0914231  12/1962  United Kingdom ................. 83/919

Primary Examiner—Daniel Wasil
Attorney, Agent, or Firm—Ronald G. Bitner

[57] ABSTRACT

A sample of the pressure tube of a CANDU type of nuclear reactor is obtained for deuterium analyses without removing the pressure tube from the reactor. The preferred sampling tool comprises two cutters and means for capturing the removed material, wherein one cutter removes the surface oxide layer, and the second cutter removes a sample for analysis. The cutters and cutting operation are designed to avoid damaging the integrity of the pressure tube to allow it to remain in service. In the preferred embodiment, the sampling tool performs the surface and sample removal operation with the fueling equipment with simple linear movement.

6 Claims, 2 Drawing Sheets

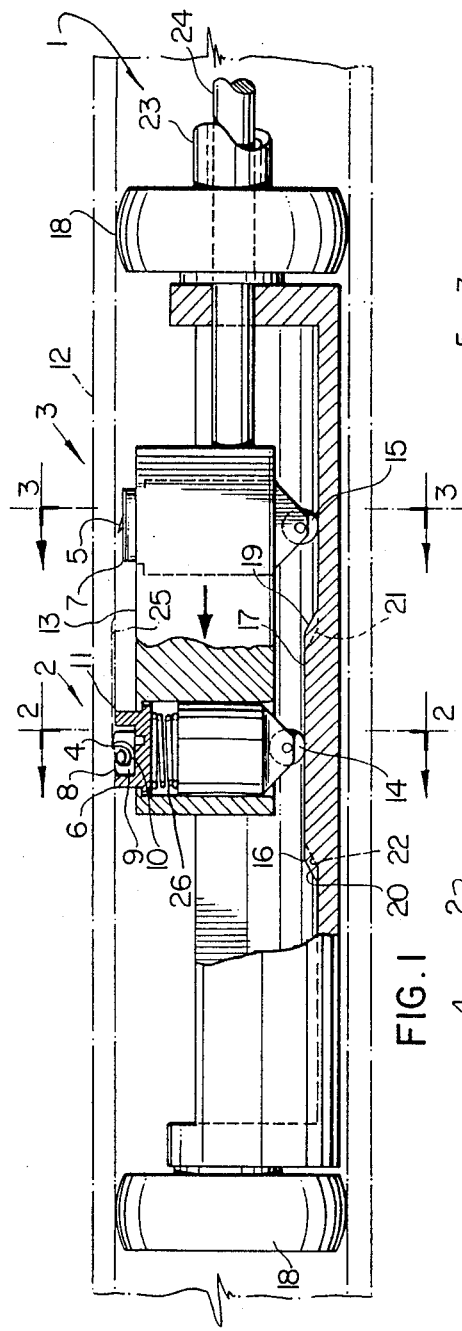
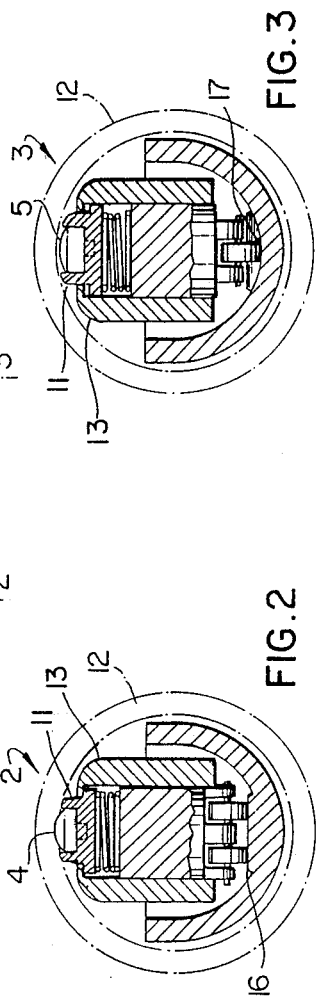

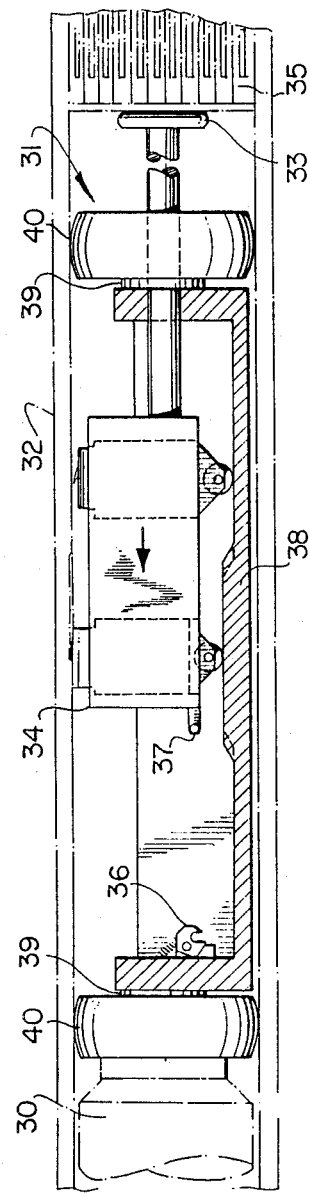

PRESSURE TUBE SAMPLING

FIELD OF THE INVENTION

This invention relates to a method and apparatus for taking samples from the pressure tubes of a nuclear reactor in-situ, and particularly for deuterium analysis.

BACKGROUND OF THE INVENTION

The present method of assessing the useful life of pressure tubes in CANDU reactors requires the periodic removal of a tube. Samples are cut from the removed tube and analyzed for deuterium content. The deuterium concentration is then used as a measure of the useful life of the remaining pressure tubes. This approach is very costly because of the long shutdown period required to remove and replace a pressure tube.

Attempting to provide in-situ sampling (without pressure tube removal) presents numerous difficulties. Obtaining a useful sample is made difficult by the hard oxidized surface, and the need to obtain sample material from beneath the surface layer. To preserve the structural integrity of the tube and avoid detrimental residual stress, the sampling depth must be controlled and sampled region must be left with smooth changes in geometry in all axes. Furthermore, the technique used for removing the surface material or sample must not involve excessive heating, as this affects the results of the subsequent analysis. Another difficulty is the recovery of the sample for analysis and preventing particles from being left in the pressure tube. Also, it is desirable to have a simple sampling device that can operate in the presence of reactor coolant and high radiation fields.

SUMMARY OF THE INVENTION

An object of the present invention is to provide in-situ sampling of the pressure tubes of a nuclear reactor.

It was found that obtaining a representative sample indicative of pressure tube condition, in-situ, for subsequent deuterium analysis, requires that the surface, in the region where the sample is to be taken, must be removed. This is because the surface contains an oxide layer, and beneath the oxide layer, it was found, is a region rich is deuterium and not representative of the deuterium content of the pressure tube as a whole. It was found that separation of the oxide and deuterium rich layers from a sample, after cutting, was impractical for the small size of sample that is desired for non-destructive testing of a pressure tube, in part due to the brittleness and curled shape of the cut sample. It was found that for the zirconium alloy pressure tubes tested, that from about 0.01 to 0.1 mm of surface material must be removed to provide access to a representative sample for analysis.

The present invention provides a method of obtaining a representative sample of pressure tube material in-situ, comprising, removing fuel from the pressure tube, providing a sampling tool, said sampling tool having surface removal means and surface material capturing means, sample removal means and sample capturing means, inserting the sampling tool in the pressure tube, removing surface material from a region of the inner surface of the pressure tube to a depth sufficient to provide access to material representative of the pressure tube, removing a sample in the region where surface material was removed whereby the geometry of the removal is such as to leave a surface that is sufficiently smooth to avoid detrimental stresses, and capturing the cut sample, and withdrawing the sampling tool with captured surface material and sample.

The present invention provides an apparatus for obtaining a sample from a pressure tube in-situ, comprising a sampling tool for insertion into a pressure tube, said sampling tool having tube follower means for engaging the inner surface of the pressure tube, surface removal means, surface material capturing means, sample removal means, and sample capturing means, manipulating means for positioning the surface removal means into engagement with the pressure tube for removal of surface material, manipulating means for positioning the sample removal means into engagement with the pressure tube in the region of surface material removal, and effecting removal of a sample.

BRIEF DESCRIPTION OF THE DRAWINGS

FIG. 1 is a schematic representation of one embodiment of a sampling tool for use with the present invention.

FIG. 2 is a section of FIG. 1, taken at 2—2.

FIG. 3 is a section of FIG. 1, taken at 3—3.

FIG. 4 is a schematic representation of another embodiment of a sampling tool for the present invention.

DESCRIPTION OF PREFERRED EMBODIMENTS

With reference to the FIGS. 1 to 3, the sampling tool 1 comprises a surface removal assembly 2 and a sample removal assembly 3. Each of the surface removal assembly 2 and sample removal assembly 3, as shown, includes a similar cutter 4 and 5, respectively. Associated with each of the assemblies 2 and 3, are surface material and sample capturing means 6 and 7, respectively, each comprising a lip portion 8 in proximity with the cutter and defining a cavity 9 for receiving and retaining surface material (10), or the sample. Each of the cutters are mounted in a pressure tube engaging shoe 11 to provide the desired depth of cut.

Surface Removal means (assembly 2) and sample removal means (assembly 3) are movably mounted on a carrier 13 and spaced from one another along a longitudinal axis parallel to the longitudinal axis of the pressure tube 12. The assemblies 2 and 3 are each movable relative to the carrier along axes normal to the longitudinal axis.

Each assembly 2 and 3 is provided with a cam follower 14 and 15, respectively, for engagement with a cam surface 16 and 17, respectively, on the body of the sampling tool.

The sampling tool 1 is provided with tube follower means 18 for positioning the tool within the pressure tube 12.

As can be seen in FIGS. 2 and 3, the cutters 4 and 5 are curved with radius of curvature sufficiently similar to that of the pressure tube so as to avoid sharp edges and stress concentration in the pressure tube after cutting the sample. For similar reasons, the cam surfaces 16 and 17 have gradual ramp portions 19 and 20, and 21 and 22, respectively, to provide a smooth cut in the longitudinal direction, as can be best seen in FIG. 1.

Preferably, the cutter assemblies will include a spring 26 to allow for irregularities in the pressure tube.

In operation, some or all of the fuel bundles are removed from the pressure tube from which a sample is to be taken. The sampling tool 1, as shown in FIG. 1, is inserted into the pressure tube 12 and moved to the desired longitudinal position within the tube, by means of suitable means (not shown) attached to member 23. Surface material is removed from the pressure tube as the carrier supporting the surface removal assembly 2 is moved longitudinally along the tube, by suitable means (not shown) attached to member 24.

As the carrier traverses, from right to left in FIG. 1, the cam follower 14 rides up ramp 19, which moves the cutter 4 into engagement with the pressure tube, and removes material as the follower rides along the raised cam surface 16 until the follower descends ramp 20, leaving recess 25 in the pressure tube 12. The surface material, which can be in the form of a curl, enters the opening between cutter 4 and lip 8, and is captured in cavity 9.

In a similar manner, the sample is removed and captured, from the same region that the surface material was removed, as the cam follower 15 for the sample removal assembly 3 rides up ramp 21 and cam surface 17.

Preferably, as is shown in FIG. 1, the cam surface 16 is longer than that of cam surface 17, providing that the sample removed by cutter 5, does not include surface material, that is, oxide or deuterium rich material. For the same reason, the sample cutter 5 will have a smaller radius of curvature than that of cutter 4, so as to avoid obtaining surface material on the edges of the sample.

Since in the case of zirconium alloy pressure tubes, the oxide layer and deuterium rich layer can extend to a depth of from about 0.01 to about 0.1 mm, the depth of surface material removal should be within this range. The depth and length of sample will be determined by the amount of material desired for analysis, with the depth being limited to avoid weakening of the pressure tube.

As an example, samples were obtained from a zirconium alloy pressure tube having a thickness of 4.2 mm. Carbide cutters having a width of 9.5 mm were mounted to obtain a cut having a depth of about 0.1 mm and a width of about 5 mm. A sample length of from 3 to 4 cm provided the desired sample weight of about 50 mg for analysis.

The embodiment as shown in FIG. 1 is adapted for both positioning of the sampling tool and effecting the cutting operation from one end of the reactor. The embodiment of FIG. 4 is adapted for a system using two fueling machines, one on each end of the reactor.

In the embodiment of FIG. 4, a fueling machine ram 30 pushes the sampling tool 31 to the desired location in the pressure tube 32, from one end of the reactor. Subsequently, a fueling machine at the other end pushes against the plunger 33 that is attached to the cutter carriage 34. The second fueling machine may push directly on the plunger 33, or, as shown, through intervening fuel bundles 35. The surface removal and sample removal operation is similar to that described above with reference to FIGS. 1 to 3. The sampling tool is shown provided with mating latching elements 36 and 37 to prevent the movement of the carriage and unwanted cutter engagement after the sampling operation is completed and while the sampling tool is being removed.

Preferably, the body 38 will be weighted, and pivotally mounted, by pivots 39, relative to the guide means 18, such that gravity can be used to establish the radial position of the cutter within the pressure tube.

It will be noted that the embodiment as shown allows that the entire sampling operation as well as sampling tool insertion and positioning to be performed by simple linear movements of a conventional fueling machine or machines. Because of the simplicity of the mechanism, and the absence of motors, or the like, in the pressure tube, the sampling operation can be readily performed with coolant present, and without shutdown of the reactor.

It will be understood that the method and apparatus may vary from that detailed above. For example, although the means for removing surface and sample material are both shown as cutters, it will be appreciated that other means may be used, for example, surface and sample removal may be preformed by shearing scraping, or the like.

Also, the specific design of the sampling tool and procedure for positioning and controling cutting will be determined by the nature of fueling machine or other manipulating device used.

We claim:

1. A sampling apparatus for obtaining a sample from a pressure tube in-situ, comprising a sampling tool for insertion into a pressure tube, said sampling tool having tube follower means for engaging the inner surface of the pressure tube, surface removal means, surface material capturing means, sample removal means, and sample capturing means, cam means for positioning the surface removal means into engagement with the pressure tube for removal of surface material, cam means for positioning the sample removal means into engagement with the pressure tube in the region of surface material removal, and effecting removal of a sample, means movably mounting the surface removal means and sample removal means on a carrier spaced from one another along a longitudinal axis parallel to the longitudinal axis of the pressure tube, and wherein the surface removal means and sample removal means are each movable relative to the carrier along axes transverse to said longitudinal axis, a first cam follower associated with said surface removal means, and a second cam follower associated with said sample removal means, said sampling tool having a cam surface for engagement by said first and second cam follower, operative such that longitudinal motion of the carrier provides transverse motion of the surface removal means and sample removal means, and wherein said cam surface comprises a linear portion and a ramp portion at each end of the linear portion operative to provide gradual transverse motion of the surface removal means and sample removal means.

2. The apparatus of claim 1, comprising a first cam surface for said first cam follower, and a second cam surface for the second cam follower.

3. The apparatus of claim 1, including a fueling machine for effecting manipulation of the sampling tool and longitudinal motion of the carrier.

4. The apparatus of claim 1, wherein the surface removal means and sample removal means comprises a cutter.

5. The apparatus of claim 4, wherein the cutter has a curved cutting edge.

6. The apparatus of claim 4, wherein the sample capturing means comprises a member, adjacent to the cutter, and which forms a lip near an edge of the cutter and which defines a cavity for receiving the sample.

* * * * *